(12) United States Patent
Bowen et al.

(10) Patent No.: US 6,782,076 B2
(45) Date of Patent: Aug. 24, 2004

(54) X-RAY TOPOGRAPHIC SYSTEM

(75) Inventors: David Keith Bowen, Denver, CO (US);
Matthew Wormington, Littleton, CO
(US); Ladislav Pina, Prague (CZ);
Petra Feichtinger, Mauerkirchen (AT)

(73) Assignee: Bede Scientific Instruments Limited,
Durham (GB)

( * ) Notice: Subject to any disclaimer, the term of this patent is extended or adjusted under 35 U.S.C. 154(b) by 0 days.

(21) Appl. No.: 10/004,785

(22) Filed: Dec. 7, 2001

(65) Prior Publication Data

US 2003/0108152 A1 Jun. 12, 2003

(51) Int. Cl.⁷ .................................. G01N 23/207
(52) U.S. Cl. ............................. 378/74; 382/131
(58) Field of Search .................. 378/74, 4, 19, 378/98.8, 84, 85, 70, 73; 382/131

(56) References Cited

U.S. PATENT DOCUMENTS

| | | | |
|---|---|---|---|
| 3,716,712 A | * 2/1973 | Piwczyk | 250/51.5 |
| 3,792,269 A | 2/1974 | Grienauer | |
| 3,982,127 A | * 9/1976 | Hartmann et al. | 250/273 |
| 4,351,063 A | 9/1982 | Dineen et al. | |
| 4,928,294 A | * 5/1990 | Beard, Jr. et al. | 378/74 |
| 5,375,156 A | * 12/1994 | Kuo-Petravic et al. | 378/9 |
| 5,418,828 A | * 5/1995 | Carpenter | 378/71 |
| 5,491,738 A | 2/1996 | Blake et al. | |
| 5,588,034 A | * 12/1996 | Bowen et al. | 378/73 |
| 5,754,620 A | * 5/1998 | Hossain et al. | 378/45 |
| 5,943,434 A | * 8/1999 | Schwarz | 382/131 |
| 6,072,854 A | * 6/2000 | Kikuchi et al. | 378/73 |
| 6,320,655 B1 | * 11/2001 | Matsushita et al. | 356/237.2 |

FOREIGN PATENT DOCUMENTS

| | | |
|---|---|---|
| DE | 196 24 094 | 6/1997 |
| JP | 03-75548 | 3/1991 |
| WO | WO98/13853 | 4/1998 |

OTHER PUBLICATIONS

G.J. Price et al., X–ray Focusing with Wolter Microchannel Plate Optics, Nuclear Instruments and Methods in Physics Research, 2002, pp. 276–289, vol. A 490, Elsevier Science B.V., Amsterdam, Holland.

* cited by examiner

*Primary Examiner*—David V. Bruce
*Assistant Examiner*—Irakli Kiknadze
(74) *Attorney, Agent, or Firm*—Burns, Doane, Swecker & Mathis, L.L.P.

(57) ABSTRACT

An X-ray topographic system comprises an X-ray generator producing a beam of X-rays impinging on a limited area of a sample such as a silicon wafer. A solid state detector is positioned to intercept the beam after transmission through or reflection from the sample. The detector has an array of pixels matching the beam area to produce a digital image of said limited area. Relative stepping motion between the X-ray generator and the sample produces a series of digital images which are combined together. In optional embodiments, an X-ray optic is interposed to produce a parallel beam to avoid image doubling, or the effect of image doubling is removed by software.

17 Claims, 7 Drawing Sheets

X-RAY TOPOGRAPHIC SYSTEM

This invention relates to an X-ray topographic system for use in examining crystal structures, for example silicon single-crystal wafers or boules for use in the production of semiconductors.

BACKGROUND TO THE INVENTION

It is known to examine, for example, silicon wafers by means of X-rays to detect flaws such as slip bands which are nucleated during the rapid thermal annealing process. Such examination has hitherto been carried out by means of a Lang camera making an exposure on film. Prior art processes have suffered from a number of disadvantages, including the large size of the camera system, limitations on the size of the wafer which can be examined, and long processing times (typically about one hour for an 8" or 200 mm wafer).

One object of the present invention is to provide an X-ray topographic system which is capable of examining large samples, typically up to 300 mm diameter, and carrying out examinations rapidly, typically 5 to 15 minutes.

SUMMARY OF THE INVENTION

Accordingly, the present invention provides an X-ray topographic system comprising:

an X-ray generator for producing a beam of X-rays directed towards a sample location; and a detector positioned to receive X-rays deflected by a sample at the sample location, the detector comprising an electronic X-ray detector having an array of pixels corresponding to the beam area.

The X-ray beam may have a relatively large divergence of up to 20 milliradians.

In one form of the invention, an X-ray optic is interposed between the X-ray generator and the sample location, and is arranged to receive said beam and to transmit the X-rays as a substantially parallel beam.

In an alternative and higher resolution form, no X-ray optic is used, and any unacceptable doubling of the image is removed or compensated by software.

The detector may be positioned to receive deflected X-rays transmitted through the sample. Alternatively, the detector may be positioned to receive deflected X-rays reflected from the sample.

The X-ray generator is preferably adapted to produce a source spot size of 100 $\mu$m or less and preferably has an exit window less than 20 mm from the target.

Preferably, the system resolution is about 25 $\mu$m or better and the detector is located 5–10 mm from the sample location.

The X-ray optic is preferably a lobster eye optic comprising a number of X-ray reflective plates set at a slight angle from each other so that the output beam is substantially parallel. Typically, the plates are about 150 $\mu$m thick and are coated with gold.

The detector is suitably a charge coupled device, most preferably a digital CCD.

The present invention also provides an X-ray topographic apparatus comprising an X-ray topographic system as defined above, stepping means for producing relative stepwise motion between the system and a sample to be inspected, the step size being a function of the beam area and spectral profile, and image processing means for reading out the pixel data of the detector between successive steps.

Other features and advantages of the present invention will be apparent from the following description and from the appended claims.

DESCRIPTION OF PREFERRED EMBODIMENTS

Embodiments of the invention will now be described, by way of example only, with reference to the drawings, in which.

EMBODIMENT OF WAFER INSPECTION SYSTEM

Figure 1:
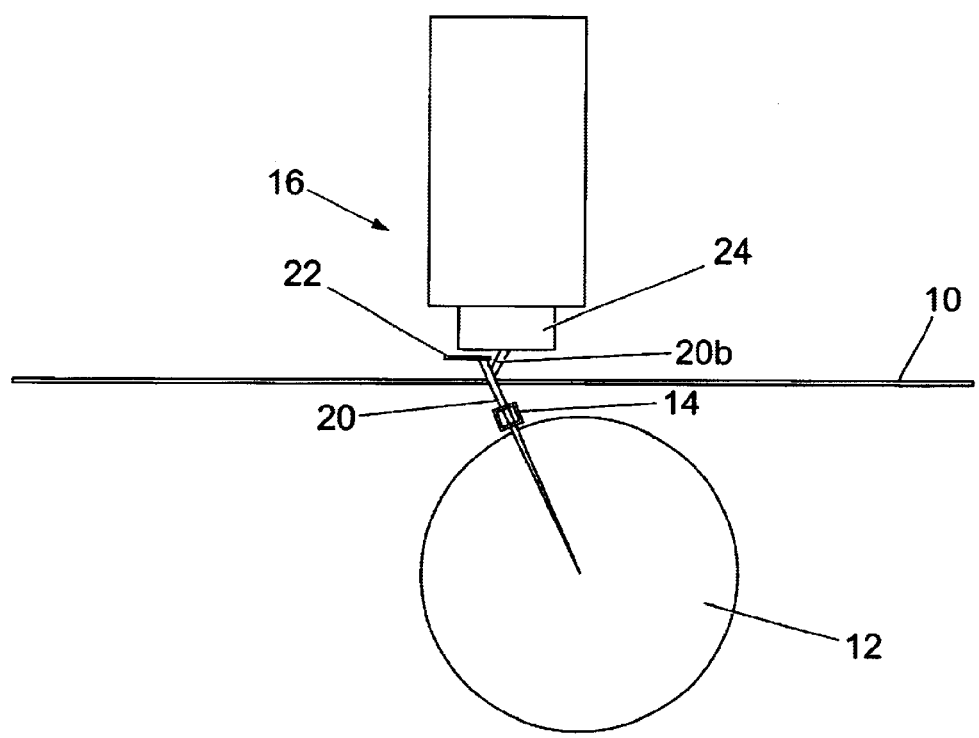
FIG. 1 is a schematic side view illustrating one system embodying the invention.
Figure 2:
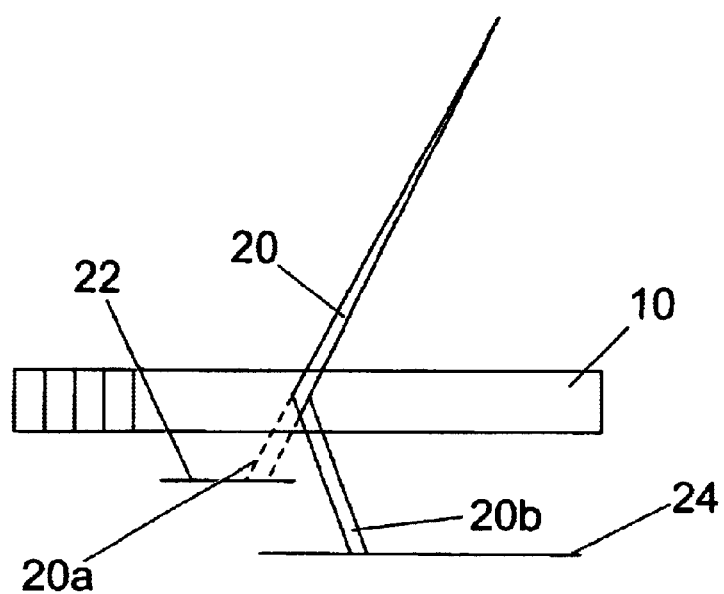
FIG. 2 illustrates the operation of the system of FIG. 1.
Figure 3:
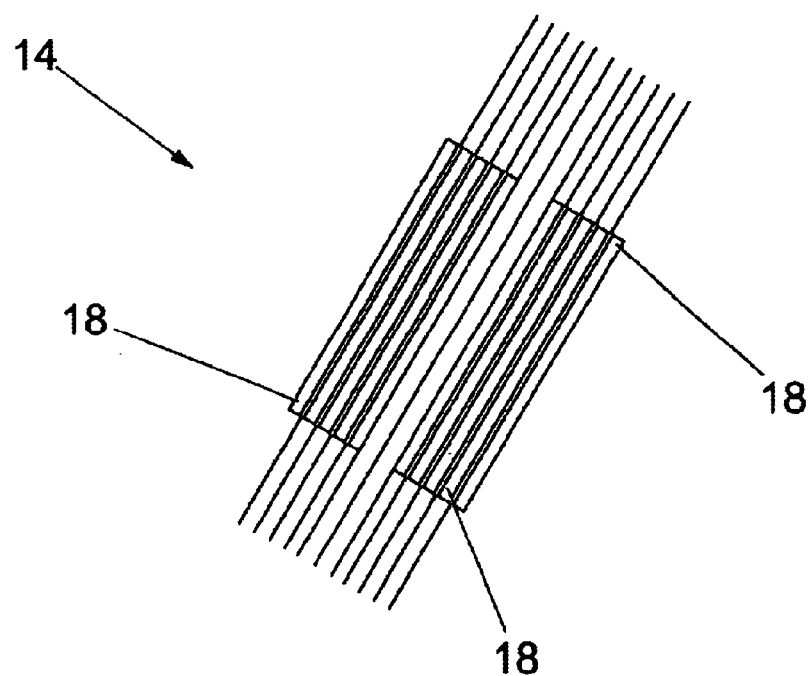
FIG. 3 shows one component of FIG. 1 in greater detail.

The embodiment of FIGS. 1 to 3 is particularly suitable for slip band detection in Si wafers up to 300 mm diameter.

Referring to FIG. 1, a silicon wafer 10 is inspected by a topographic system comprising an X-ray generator 12, an X-ray optic element 14, and a detector indicated generally at 16.

The X-ray generator 12 is most suitably the Microsource® X-ray generator from Bede plc of Bowburn, Co. Durham, which is the subject of WO 98/13853. Briefly stated, the Microsource® generator comprises an evacuated X-ray tube with external focussing coils arranged to produce a spot X-ray source on the target of 100 $\mu$m or less, and a configuration where the X-ray exit window is within 5–10 mm of the target. The Microsource® generator is particularly suitable for use in the present invention, since it enables an X-ray optic to be positioned close to the small target spot while at the same time delivering a narrowly diverging beam to the optic.

The X-ray optical element 16 is any suitable element which will accept slightly divergent rays from the generator 12 and provide as output an area of parallel X-rays. The preferred element, as used in this embodiment, is a "lobster eye" optic; X-ray optics of this type have been described in the prior art, but only in relation to use in X-ray astronomy.

As seen in FIG. 3, the lobster eye optic 14 comprises a series of flat plates 18 acting as specular reflectors and mounted to be accurately radially divergent from a point half way between the point source and the mid point of each reflector. In the preferred embodiment, the X-rays are copper K radiation, the plates 18 are gold coated and are about 150 $\mu$m thick, 6×30 mm in area, and with 80% average reflectivity. Using a total of fourteen plates, which is the practical maximum that can be accommodated with the above thickness, gives a theoretical gain of 1+14×0.8=12 approximately.

Reverting to FIG. 1, the output from the lobster eye optic 14 is a substantially parallel beam 20 which is incident on the wafer 10. The undeflected beam 20a is intercepted by a beam stop 22. The deflected beam 20b is incident on an electronic detector element 24 which will be described below.

More specifically, the beam 20 has a divergence of about 2 mr and is segmented into a number of stripes, about 30 mm long. Each stripe is polychromatic and gives rise to a Kα1, Kα2 stripe on the image (see FIG. 2). Hence the image from one stripe will be doubled.

In the usual method of Lang topography, the specimen and the photographic plate are translated together through the beam. A defect is seen twice, once by the Kα1 beam and later, after the plate has translated, by the Kα2 beam. Because the distance from the specimen to the film is at least 50 mm for a large wafer, and the divergence between Kα1 and Kα2 is about $2.5 \times 10^{-3}$, the image is doubled (by $50 \times 2.5 \times 10^{-3} = 0.125$ mm) and a slit, rather than just a stop, is used to select only the Kα1 beam.

In the present arrangement, the image is not doubled when the wafer 10 is static; the Kα2 is simply of weaker intensity, and other components from Bremsstrahlung are also there without any image multiplication. This is actually a spectrally-reduced segment of a white radiation topograph.

If now we translate the wafer 10 by a step, we will get a faithful image of the part of the specimen that is now struck by the beam. With a film detector this would of course be superimposed on the first image. However, by using an electronic detector element 24 it is possible to store the images from successive steps electronically to produce an image for the entire wafer 10.

As long as all of the wafer 10 is scanned uniformly by all of the beam, it does not matter what is the intensity profile in the beam. The basic requirement for the optic 14 is that as much intensity as possible is reflected/scattered parallel to the original direct beam.

It is extremely desirable that the generator 12 provides a "point" (as discussed below) source. A line source perpendicular to the plane of FIG. 2 will give coma in the same direction, and a line source parallel to the plane of FIG. 2 and to the wafer will give doubled images from the Kα1, Kα2 components.

Turning to questions of resolution and source size, the usual equation for resolution, d, applies:

$$d = hb/a$$

where a and b are as defined in FIG. 2, and h is the source dimension perpendicular to the Figure. In the arrangement of FIG. 1, the dimensions of the Microsource® X-ray source determine a as no smaller than 75 mm, and b could readily be 15 mm.

X-ray topographers have customarily striven to meet a target of 1 μm resolution, which may be desirable for academic research but involves very long (days) exposure and processing time. Since the potential exposure reduces as the square of resolution, huge gains can be made by relaxing the target resolution. For use in the inspection and quality control of semiconductor materials, it is necessary to see isolated dislocations, but not the details of their interactions. We have concluded that a resolution of 25 μm is ample for this, and indeed up to 100 μm could be usable.

Aiming for 25 μm resolution implies an X-ray source spot of 125 μm. Considerations of coupling to an optic could limit the spot size to 100 μm which in the Microsource® generator could be run at 100 W, and give a resolution of 20 μm on the detector screen.

There is still a risk of image doubling from the Kα doublet, since the beams will still diverge from a defect position by $10^{-3}$ on their way to the detector. However, if the detector is within 10 mm of the wafer the blurring will only be 25 μm, which is acceptable, and it should be possible to achieve a distance of 2–5 mm between sample and detector.

For the above-described embodiment and benchmark measurements, we have calculated that the exposure time for examining a 8" (200 mm) Si wafer, using 100 W on a Cu target, would be in the region of 5–10 minutes. In contrast, a known system uses 2.5 m between source and wafer with image capture on film, 15 kw source power, and 1 hour exposure time. It also requires photographic film processing.

Considering now the detector 16, the basic requirement is a detector which gives an electric signal output of received X-ray intensity in a pixel array. The preferred detector is a digital CCD detector in a rectangular configuration, e.g. 2000 by 200 pixels. Such detectors are available with a resolution from 24 down to about 7.5 μm. The use of a detector of this aspect ratio allows the detector to be placed very close to the wafer. A less sophisticated alternative is the Photonic Science Hires detector which can be configured to give 30 μm resolution over about 12×15 mm, or 15 μm resolution over 6×7.5 mm.

Embodiment of Wafer Inspection Apparatus

Figure 4:
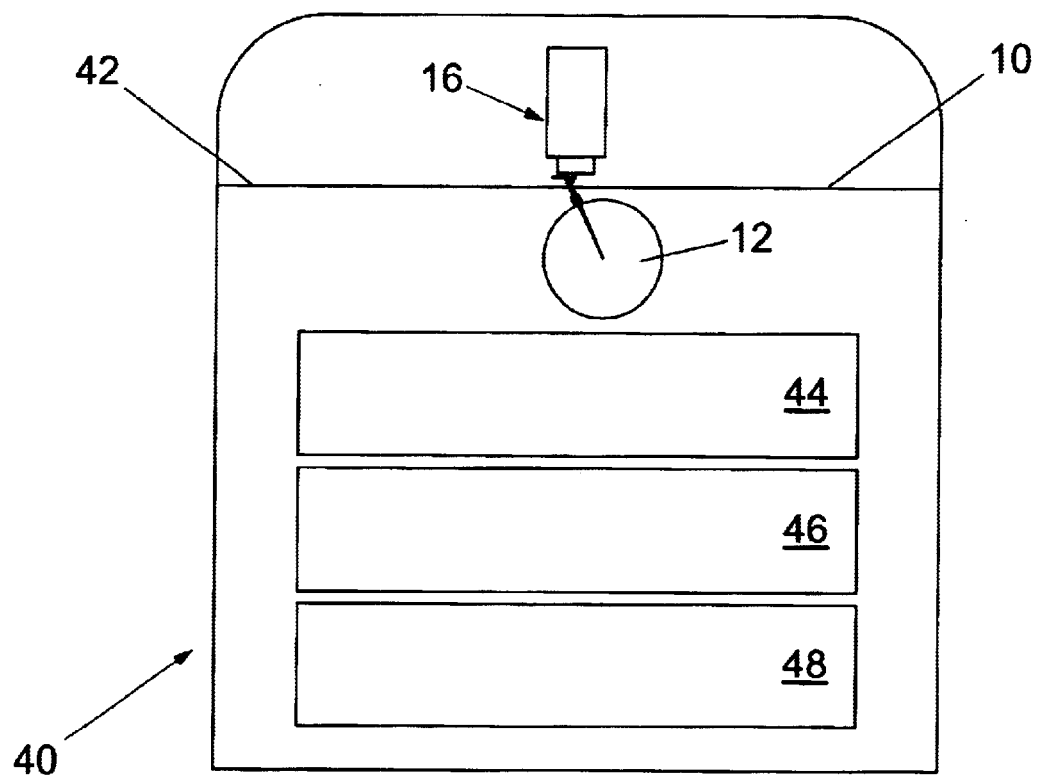
FIG. 4 is a schematic representation of an apparatus incorporating the system of FIG. 1.

Turning now to FIG. 4, there is schematically depicted an apparatus, incorporating the foregoing system, for inspection of wafers. The apparatus 40 includes an XY table 42 driven along orthogonal axes by servomotors (not shown) in known manner, a Microsource® controller 44, an interlock controller 46, and a servomotor controller 48. The apparatus 40 is of compact dimensions, typically about 650 mm wide by 750 mm high.

Embodiment of Boule Inspection by Reflection

Figure 5:
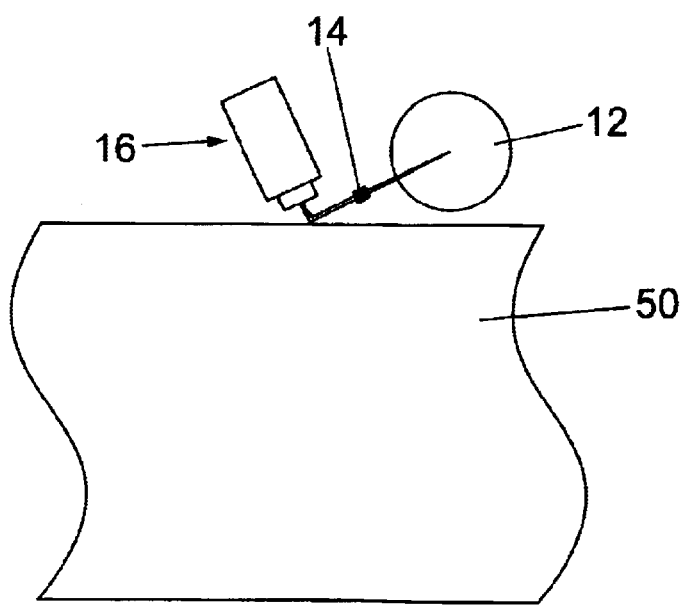
FIG. 5 illustrates an alternative form of apparatus.

The invention as thus far described operates in transmission. It may equally be used in a reflection mode, either with wafers or, as illustrated in FIG. 5, with a boule 50. A Si boule may typically be 300 mm diameter by about 1 m length. The entire boule or selected parts only may be inspected by providing servomotor drives to produce stepwise relative motion between the boule 50 and the inspection system 10, 12, 14 in rotation and axially. Again, the requirement is to acquire a digital representation by stepping the detector across the area of interest.

It will be understood that the image data at each step is read out and used to build up an image of the entire area inspected. Typically, the value for each pixel will be stored in a corresponding memory location until the entire image can be displayed on a screen or printed. It may be necessary to use commercially available image processing software to normalise image intensities and to merge the images from the separate steps together.

Embodiment of System without X-ray Optic

Figure 6:
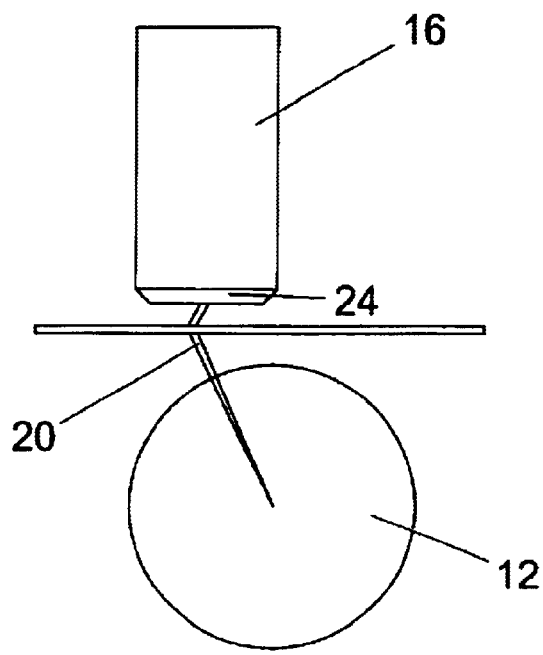
FIG. 6 illustrates a modified system without an x-ray optic.

Turning now to FIG. 6, a modified form of the present invention will be discussed. FIG. 6 is similar to FIG. 1 and similar parts are denoted by like reference numerals. In FIG. 6, however, the X-ray optic such as lobster eye optic 14 is omitted. This has the result that the X-ray beam 20 reaching the sample 10 is more divergent than in the previous embodiments, and the radiation deflected by thew sample has a broader spectral range. When an optic is used the divergence can in practice be limited to about 2 mr. When no optic is used, the divergence depends on the nature and operating conditions of the X-ray source, but typically a relatively large divergence of up to 20 mr may be used.

In one example of such an arrangement, a Microsource® generator was used with a copper anode. The x-ray imaging system was a Photonic Science imager with 512×512 pixels each with a nominal size of 30×30 µm. This was connected to a 700 MHz Pentium III based PC with 128 Mbytes of RAM, and using a PCVision frame grabber.

Figure 7:
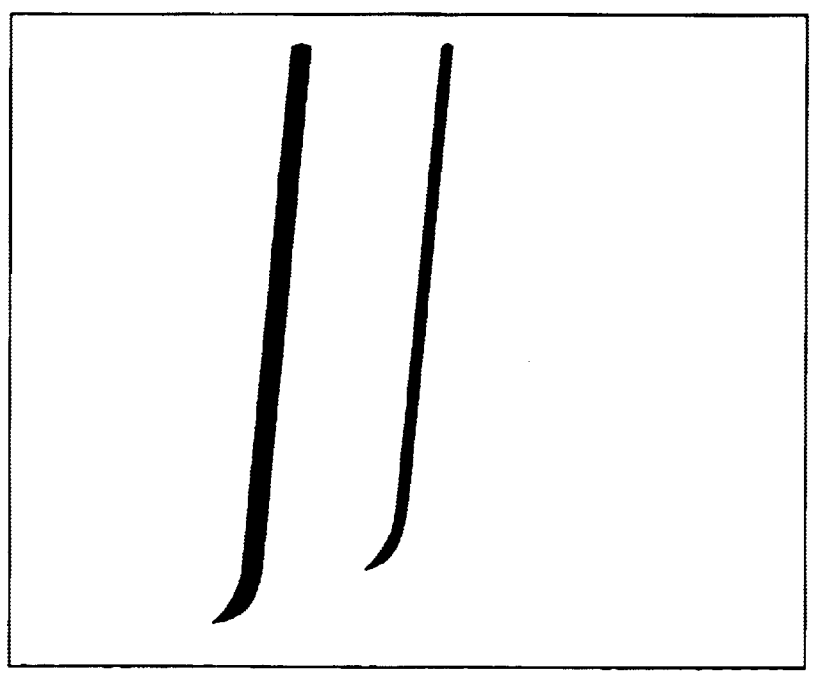
FIG. 7 is an example of an image obtained by a system embodying the invention.

FIG. 7 is a representation of one image obtained from the arrangement of FIG. 6 examining an edge region of a silicon wafer. This shows two diffraction streaks from the 115 glancing incidence Bragg reflection from a Si (001) sample. The left and right streaks are respectively $K\alpha 1$ and $K\alpha 2$ diffraction streaks. The streaks are curved at the bottom due to the curved edge of the sample. A defect is visible about ⅔ of the way down from the top of the $K\alpha 1$ streak as a bright white region.

In the embodiments of FIGS. 1 to 5, the $K\alpha 1$ and $K\alpha 2$ diffraction streaks, due to the presence of the optic, are sufficiently close together to be treated as a single image for most purposes. In the present embodiment this may be possible for some less critical applications, but if not then the images produced by the detector can be manipulated by software.

For any known specimen-detector distance there is a known divergence of the $K\alpha 1$ and $K\alpha 2$ beams. This in effect gives a slight magnification of the image, and can be corrected completely by demagnifying the image in one dimension only (in the incidence plane). This removes completely the effects of the spectral distribution upon the resolution, which thus becomes limited only by the detector resolution, which is expected to improve with progress in the semiconductor technology, and can be sub-micron. However, this correction will not be possible where the specimen is not reasonably planar.

As an alternative, or where there is a bent or distorted specimen, the $K\alpha 1$ and $K\alpha 2$ images can be separated in the software and processed to maintain resolution and intensity, as described below.

The foregoing description has assumed a single exposure at each step of the sample. However, currently available electronic X-ray detectors are not sufficiently sensitive to allow such operation, which would result in an unacceptable signal to noise ratio. It is convenient to use a detector such as a CCD detector operating in a conventional raster scan such as 525 lines at 60 Hz or 625 lines at 50 Hz. In this case, a significant number of frames of the same sample area will have to be integrated, i.e. a cumulative sum taken for each pixel. With available technology it may be necessary to integrate between 10 and 2000 frames before stepping to the next area of the sample.

Examples of Software

There now follows one example of software by which a number of frames in a wider format can be integrated.

Integrating Image

This example employs an algorithm as shown in FIG. 6 and further described as follows (text in a bold font refer to variables defined in the program source code):

1. The routine is initialised by creating a 32-bit floating point image (im_expose) and an 8-bit (byte) image (im_temp). The X-ray imaging system, assumed to be connected to channel 0 of the PCVision card, is selected as the video source.
2. Acquire (snap) a single frame from the X-ray imaging system into the byte image, im_temp.
3. If the gray scale exposure type is selected continue to step 4. If the binary threshold exposure type is selected, convert the current frame, im_temp, to a two-level (binary) image. Pixel values in im_temp below the specified threshold limit are set to zero (black) whereas pixel values above the threshold value are set to 255 (white).
4. Add the current frame, im_temp, to the integrated image, im_expose. A 32-bit floating point image is used to store the integrated image so as to avoid overflow problems. The image im_temp is added to im_expose on a pixel-by-pixel basis. The resultant image is multiplied by a scaling factor, which in this case is set equal to 1.0.
5. Repeat steps 2–4 until the specified number of frames, designated by the Frames variable, is integrated.
6. Finally, convert the 32-bit floating point image im_expose to an 8-bit byte image. In order to convert between 32-bit and 8-bit image formats the pixel values are scaled to map to the value range 0 to 255. This scaling can be achieved in three ways: a) by dividing im_expose by the number of frames integrated. b) automatically based on the minimum and maximum pixel values and c) by adding an offset and multiplying by a scale factor. In the latter case, values that are still outside the 0 to 255 range are clipped. Pixel values less than 0 are set equal to 0 while those greater than 255 are set to a value of 255.
7. Save the final 8-bit integrated image to a disk file with a specified name.
8. Display the integrated image in the main program window.

Combined Integrated Images

The integrated images acquired according to the algorithm described in the previous section contain $K\alpha 1$ and $K\alpha 2$ diffraction streaks respectively from positions $(\chi 1, \gamma 1)$ and $(\chi 2, \gamma 2)$ on the sample. The Tile command combines a distribution over an extended region.

In order to understand the Tile algorithm, we must define the coordinate spaces used to describe the location of pixels within an image and the location and size of a rectangular region of interest (RROI) within an image. It is also important to define the transformation that maps a spatial coordinate $(\chi, \gamma)$ on the sample to a pixel coordinate in an image or RROI.

Referring to FIG. 7, the origin of an image has the coordinates (0,0) and refers to the pixel at the top, left-hand corner of the image. The horizontal side of the image is denoted by X and the vertical side of the image by Y. Hence, the pixel at the bottom, right-hand corner of the master image has the coordinates (X,Y).

The origin of a RROI has the coordinates (x,y) relative to the origin of its parent image. The horizontal extent of an RROI is denoted by dx and the vertical extent by dy. Hence, the pixel at the bottom, right-hand corner of an RROI has the coordinates (x+dx, y+dy) relative to the origin of its parent image.

FIG. 7 shows the relationship between the coordinates of an image and an RROI. The equations used to transform between world coordinates (x,y) and RROI coordinates (x,y) within an image expressed as follows $$x=(x-xo)/dx$$

$$y=(y-yo)/dy$$

where (xo,yo) is the origin expressed in world coordinates and dx and dy are the pixel dimensions of the X-ray imaging camera in the x-(horizontal) and y-(vertical) directions, respectively. Here we have assumed that the senses of the x- and y-directions are identical to those within the image. The pixel coordinates for both images and RROI's are arranged such that the x-ordinate increases from left to right (horizontal). The y-ordinate increases from top to bottom (vertical).

Figure 8:
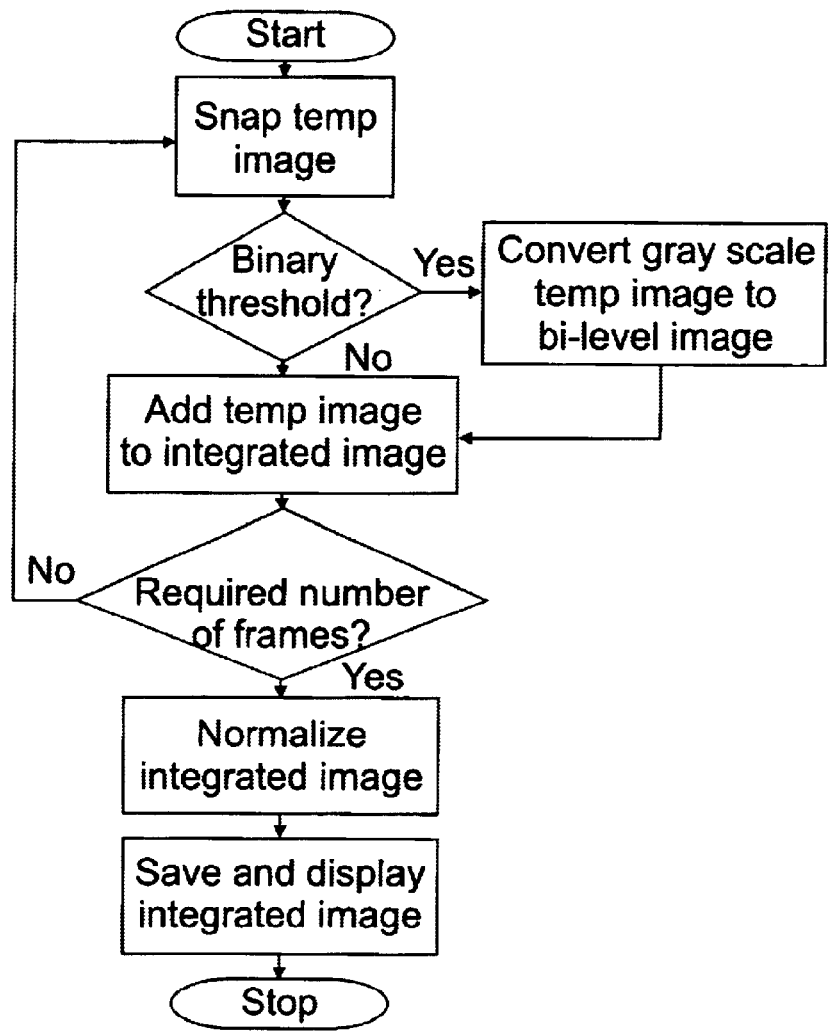
FIG. 8 is a flow chart of an algorithm used in one form of the invention.
Figure 9:
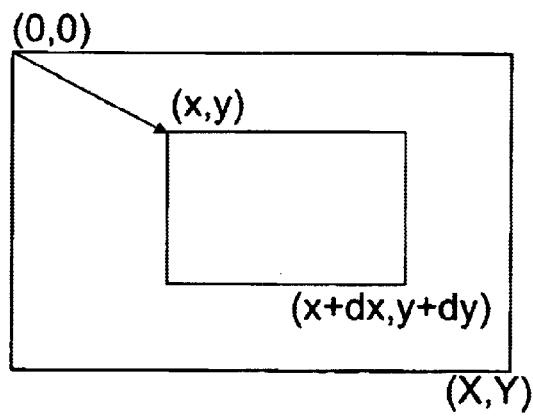
FIG. 9 illustrates geometric coordinates used in combining images.
Figure 10:
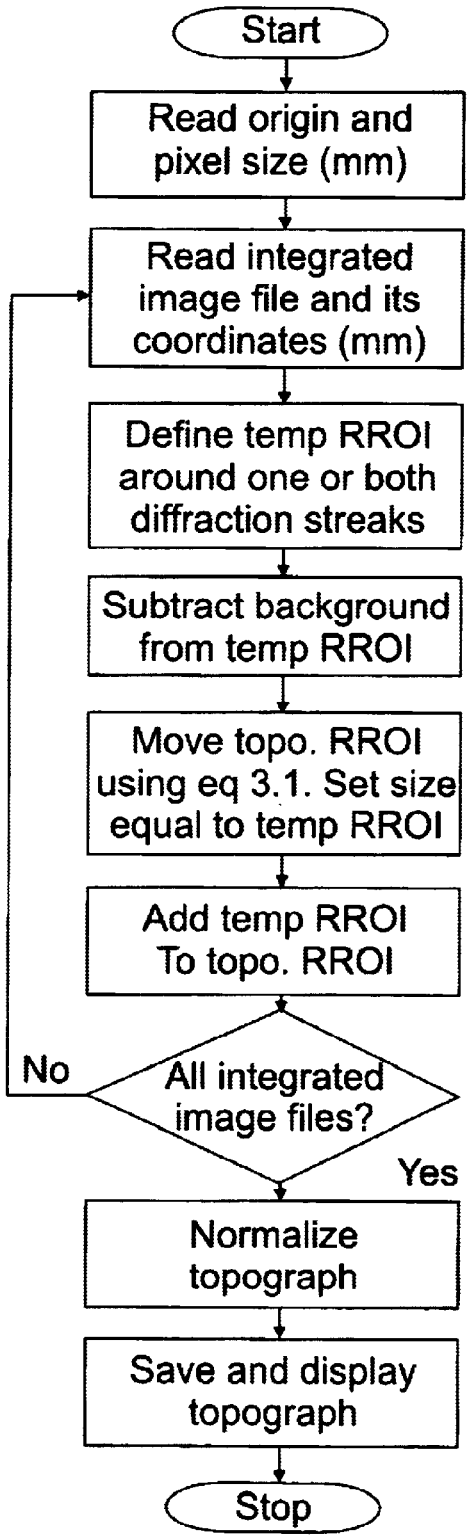
FIG. 10 is a flow chart of an algorithm used in combining images.

The algorithm employed by the Tile command is shown in FIG. 8 and further described as follows (text in bold font refer to variables defined in the program source code):

1. The routine is initialised by creating a 32-bit floating point image (im_tile) and rectangular region of interest (RROI) within this image (rroi_tile). The X-ray imaging system, assumed to be connected to channel 0 of the PCVision card, is selected as the video source.
2. From a user selected.ini file, read the origin (OriginX, OriginY) and horizontal and vertical pixel sized, denoted by ScaleX and ScaleY, respectively in world coordinates.
3. Read the position (x,y) and horizontal and vertical dimensions denoted dx and dy, respectively from the .ini file. These values are in world units (typically mm). Also read the name of the integrated image file associated with this world position.
4. Create a temporary 8-bit image, im_temp, and read the file obtained in step 3 into this image.
5. Create RROI within the temporary image, rroi_temp. The starting position and size of rroi_temp is selected to include one, or both, of the diffraction streaks.
6. Subtract a constant value from im_temp on a pixel-by-pixel basis, the constant value being the average pixel value within a region far from either one of the diffraction streaks, i.e. the background pixel value.
7. Move the RROI rroi-tile according to equation 1.1. Adjust the size of the rro1.tile to match that of rroi_temp.
9. Add the RROI, rroi_temp, to the topograph RROI, rror_tile. A 32-bit floating point image is used to store the topograph so as to avoid overflow problems. The image rroi_temp is added to rroi_tile on a pixel-by-pixel basis. The resultant image is multiplied by a scaling factor, which in this case is set equal to 1.0.
10. Delete the temporary image, im_temp, and RROI, rroi_temp.
11. Repeat steps 3–9 until all integrated image files in the user selected .ini file have been processed.
12. Convert the 32-bit floating point image im_tile to an 8-bit byte image. In order to convert between 32-bit and 8-bit image formats the pixel values are scaled to map to the value range 0 to 255. This scaling can be achieved in three: a) by dividing im_expose by the number of frames integrated. b) automatically based on the minimum and maximum pixel values and c) by adding an offset and multiplying by a scale factor. In the latter case, values that are still outside the 0 to 255 range are clipped. Pixel values less than 0 are set equal to 0 while those greater than 255 are set to a value of 255.
13. Save the final 8-bit integrated image to image to a disk file with a specified name.
14. Delete the image im_tile and associated RROI, rroi_tile.
15. Finally, display the integrated image in the main program window.

Examples of Expose and Tile

Figure 11:
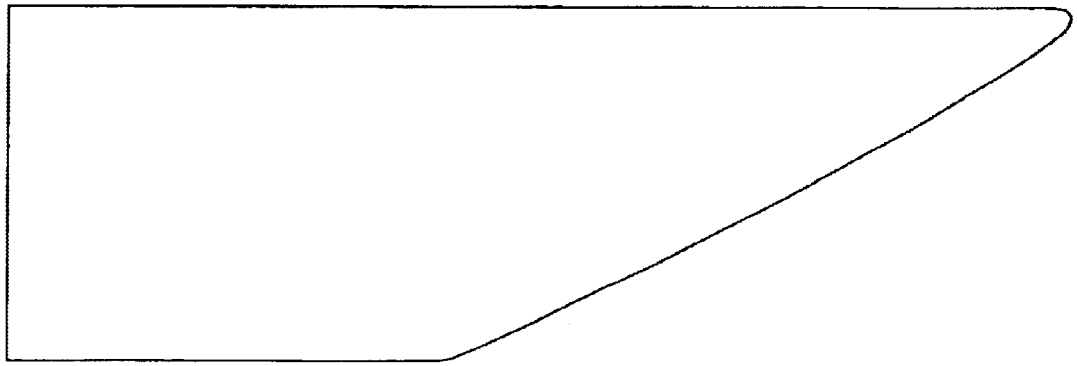
FIGS. 11 and 12 are examples of combined images.
Figure 12:
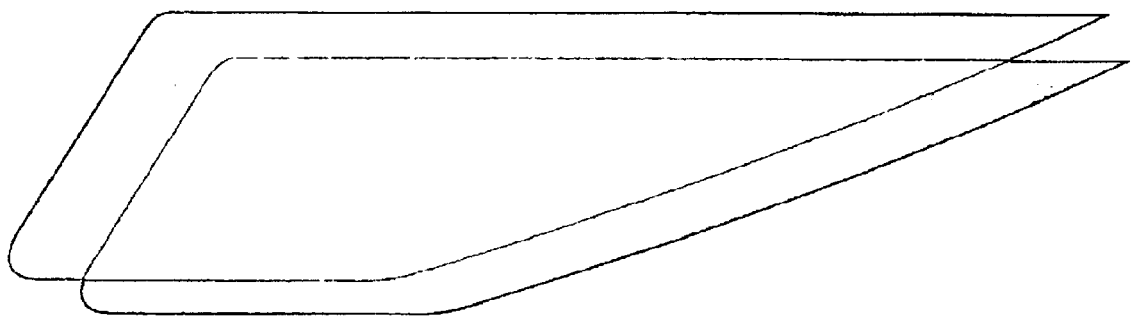

FIGS. 11 and 12 show selected reflection topographs created using the Expose and Tile commands described above. All of the topographs have been inverted to facilitate comparison with conventional X-ray topography. White regions are those areas that weakly diffract X-rays whereas black regions are those that diffract strongly.

FIGS. 11 and 12 show a reflection topograph produced using both the $K\alpha 1$ and $K\alpha 2$ diffraction streaks. Integrated images were collected at a horizontal interval of 0.1 mm with 250 frames integrated in each image (this corresponds to an acquisition time of about 12 secs per image). A pixel size of 0.28 mm was used instead of the nominal value of 0.30 mm as this resulted in the sharpest topographs.

When acquiring the integrated images used to create the topograph shown in FIG. 11, the sample was accurately aligned such that the diffraction streaks were vertical. This is not the case with the integrated image shown in FIG. 12. In this case, we immediately see that the diffraction streaks are inclined a few degrees away from the vertical direction. This was due to the tilt ($\chi$-axis) of the sample being improperly adjusted with respect to the incident X-ray beam. For flat samples it is easy to align the sample such that the diffraction streaks are vertical. However macroscopically bent or distorted sample may lead to diffraction streaks that are inclined to the vertical direction. If this is indeed the case, the final topograph will be blurred or contain ghost images due to the $K\alpha 1$ and $K\alpha 2$ radiation not overlapping. A rather contrived example of this effect is shown in FIG. 12. This topograph was created using both the $K\alpha 1$ and $K\alpha 2$ diffraction streaks with the $\chi$-axis adjusted so that these streaks were several degrees away from the vertical direction.

In order to remove the blurring of a topograph from a poorly aligned or macroscopically bent sample, we could of course use only the $K\alpha 1$ diffraction streak to create the topograph. However, in doing this we would neglect ⅓ of the available intensity i.e. the intensity contained in the $K\alpha 2$ diffraction streak. Furthermore, this procedure would not correct the geometric distortion (slanting) of the topograph which is also apparent in FIG. 12.

Addition of $K\alpha$ and $K\alpha 2$ Images

To create a topograph using all of the available intensity without any blurring or geometric distortions we propose the following modification to the basic Tile algorithm described above.

1. Create a topograph using the basic Tile algorithm with the RROI in each integrated image defined so as to include only the $K\alpha 1$ diffraction streak.
2. Repeat step 1 but define the RROI so as to include only the $K\alpha 2$ diffraction streak.
3. Perform affine transformations on the topographs created in steps 1 and 2 so as to map the $K\alpha 1$ and $K\alpha 2$ images on top of one another.
4. Add the transformed $K\alpha 1$ and $K\alpha 2$ topographs together.

Here, an affine transformation is a generalised name for as yet unspecified translation, rotation and shear image processing operations.

To determine and correct the angle $\alpha$ at which the diffraction streaks are inclined to the vertical direction we propose the following simple scheme. First we define two RROI's at the top and bottom few percent of an integrated image. These RROI's are then projected onto the horizontal axis, that is the pixel values are summed along a horizontal line in the image. The x-positions of the maximum pixel values (by fitting the projection to a peak function to obtain sub-pixel accuracy) at the top and the bottom of the image could be fitted to a linear equation (straight line through the two points) to determine $\alpha$. This procedure would be repeated for all integrated images comprising the final topograph. The image is then sheared by another affine transformation that corrects the value of $\alpha$ to zero, before performing the stepwise integration.

Modifications

Modifications may be made to the above embodiments.

It is possible to use X-ray optics other than lobster eye optics, provided a substantially parallel output is obtained.

For example, parabolic specular or multilayer optics could be used, particularly parabolic graded multilayers, but these are likely to be more expensive than lobster eye optics.

The aperture on either side of the optic could be extended by using non-graded multilayer plates, or still further by using crystal reflectors such as mica.

The width of 30 mm is believed to be a practical limit to lobster eye optics at present. The Microsource® generator can provide a total aperture of 40–45 mm at a distance of 50 mm, and so if a wider optic could be made the exposure could be decreased in proportion.

The use of a less sophisticated optic than that described would also give a useful, though somewhat poorer, performance. Even a lobster eye optic of only two plates would give a gain of 2.6× and a processing time for a 8" wafer of 20–25 mins.

The use of the Microsource® X-ray generator is preferred for two reasons. One is the ability to place the optic very close to the X-ray source. The other is that the power and source size can be controlled electronically to alter the tradeoff between resolution and throughput according to the needs of the measurement, with no mechanical alterations. The latter factor also makes it possible to scan the sample at relatively low resolution to detect areas with some discrepancy, and then to inspect such areas in greater detail.

However, the invention is not limited to the use of the Microsource® generator, and other means of producing X-rays may be used.

Although described with reference to the detection of slip bands in Si, the invention is useful with other materials, such as defect detection in EUV optical material such as CaF2 and in SiC and III–V crystals.

Other modifications and improvements may be made within the scope of the invention.

What is claimed is:

1. An X-ray topographic system comprising:
   an X-ray generator for producing a beam of X-rays directed towards a sample location; and a detector positioned to receive X-rays deflected by a sample at the sample location, the detector comprising an electronic X-ray detector having an array of pixels corresponding to the beam area at the detector; and
   an image processing means for reading out the pixel data of the detector to thereby generate an image of the sample, wherein the beam of X-rays has sufficient divergence to produce doubling of the image at the detector, and wherein the image processing means is operative to remove effects of said image doubling.

2. A system according to claim 1, in which the beam has a divergence of up to 20 milliradians.

3. A system according to claim 1, including an X-ray optic interposed between the X-ray generator and the sample location, and arranged to receive said beam and to transmit the X-rays as a substantially parallel beam.

4. A system according to claim 3, in which the X-ray optic is a lobster eye optic comprising a number of parallel, X-ray reflective plates.

5. A system according to claim 4, in which the plates are about 150 $\mu$m thick and are coated with gold.

6. A system according to claim 1, in which the detector is positioned to receive deflected X-rays transmitted through the sample.

7. A system according to claim 1, in which the detector is positioned to receive deflected X-rays reflected from the sample.

8. A system according to claim 1, in which the X-ray generator is adapted to produce a source spot size of 100 $\mu$m or less.

9. A system according to claim 8, wherein said X-ray generator has an exit window less than 20 mm from the sample.

10. A system according to claim 8, in which the system resolution is about 25 $\mu$m and the detector is located 51–10 mm from the sample location.

11. A system according to claim 1, in which the detector is a charge coupled device.

12. An X-ray topographic apparatus comprising an X-ray topographic system according to claim 1, and stepping means for producing relative stepwise motion between the system and a sample to be inspected, the step size being a function of the beam area.

13. Apparatus according to claim 12, in which the stepping means comprises an XY table movable with respect to the X-ray generator and the detector, and a pair of servomotors arranged to step the XY table in orthogonal directions.

14. Apparatus according to claim 12, in which the stepping means comprises a boule transport device arranged to rotate and axially translate a boule with respect to the X-ray generator and the detector, and a pair of servomotors arranged to step the boule transport device in rotation and translation.

15. Apparatus according to claim 12, in which the image processing means comprises means for storing the pixel data output from each step, and means for combining data from successive steps to form a composite image.

16. Apparatus according to claim 12, in which the detector operates in raster scant and the image for each step is derived by integrating a plurality of scanning frames.

17. A system according to claim 1, wherein the X-ray generator generates K$\alpha$1 and K$\alpha$2 radiation which is deflected by the sample and received by the electronic X-ray detector.

* * * * *